United States Patent
Ochiai

(10) Patent No.: US 12,016,984 B2
(45) Date of Patent: Jun. 25, 2024

(54) NEGATIVE PRESSURE TRANSMITTER AND BREAST PUMP DEVICE USING SAME

(71) Applicant: PIGEON CORPORATION, Tokyo (JP)

(72) Inventor: Yukifumi Ochiai, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 1010 days.

(21) Appl. No.: 16/625,209

(22) PCT Filed: Jun. 22, 2018

(86) PCT No.: PCT/JP2018/023871
§ 371 (c)(1),
(2) Date: Dec. 20, 2019

(87) PCT Pub. No.: WO2019/004094
PCT Pub. Date: Jan. 3, 2019

(65) Prior Publication Data
US 2020/0139027 A1 May 7, 2020

(30) Foreign Application Priority Data
Jun. 30, 2017 (JP) .................................. 2017-128899

(51) Int. Cl.
*A61M 1/06* (2006.01)
*A61M 1/00* (2006.01)

(52) U.S. Cl.
CPC .............. *A61M 1/062* (2014.02); *A61M 1/06* (2013.01); *A61M 1/064* (2014.02); *A61M 1/82* (2021.05);
(Continued)

(58) Field of Classification Search
CPC ........ A61M 1/06; A61M 1/062; A61M 1/064; A61M 1/066; A61M 1/068; A61M 1/007;
(Continued)

(56) References Cited

U.S. PATENT DOCUMENTS

| | | | |
|---|---|---|---|
| 2011/0098639 A1* | 4/2011 | Kirchner | A61M 1/062 604/74 |
| 2014/0121593 A1* | 5/2014 | Felber | A61M 1/0697 604/74 |
| 2016/0228624 A1* | 8/2016 | Holtz | B01D 19/0031 |

FOREIGN PATENT DOCUMENTS

| | | |
|---|---|---|
| CN | 101980922 A | 2/2011 |
| JP | S4736526 Y1 | 11/1972 |

(Continued)

OTHER PUBLICATIONS

Written opinion of PCT/JP2018/023871 mailed Aug. 21, 2018 and English translation thereof.
(Continued)

*Primary Examiner* — Shefali D Patel
*Assistant Examiner* — William R Frehe
(74) *Attorney, Agent, or Firm* — Muncy, Geissler, Olds & Lowe, P.C.

(57) ABSTRACT

The present invention provides a negative pressure generator such as a suction cup, the negative pressure generator comprising a negative pressure transmitter with a shape that remains constant after deformation so that no part of the negative pressure transmitter comes into contact with another member of the negative pressure generator.

The negative pressure transmitter (80) includes an opening (81), a closed bottom portion (83), and an intermediate portion (82) connecting the opening to the bottom portion, wherein the intermediate portion includes at least a plurality of rigid portions (84*a*) that are formed at predetermined intervals so as to inhibit deformation, and flexible portions (86*a*) that are formed between the plurality of rigid portions and formed from a flexible material.

11 Claims, 9 Drawing Sheets

(52) U.S. Cl.
CPC ..... *A61M 1/0697* (2021.05); *A61M 2205/502* (2013.01)

(58) Field of Classification Search
CPC ........ A61M 2210/1007; A61M 1/0697; A61M 1/82; A61M 2205/07; A61M 1/067; A61M 1/069; A61M 1/0693; A61M 1/06935; A61B 2018/00333; A61J 13/00
See application file for complete search history.

(56) References Cited

FOREIGN PATENT DOCUMENTS

| | | |
|---|---|---|
| JP | 2005088979 A | 4/2005 |
| JP | 2007-330703 A | 12/2007 |
| JP | 2008213854 A | 9/2008 |
| KR | 2013-0000825 A | 1/2013 |
| WO | 2018/009449 A1 | 1/2018 |

OTHER PUBLICATIONS

English Translation of International Search Report of PCT/JP2018/023871 mailed Aug. 21, 2018.
Written opinion of PCT/JP2018/023871 mailed Aug. 21, 2018.
The extended European search report for the corresponding EP application No. EP18823470 mailed Feb. 22, 2021.
The office action for the corresponding CN application No. 201880042370.8 mailed Apr. 25, 2022 and machine translation thereof.

* cited by examiner

NEGATIVE PRESSURE TRANSMITTER AND BREAST PUMP DEVICE USING SAME

TECHNICAL FIELD

The present invention relates to a negative pressure transmitter used when a mother or the like pumps breast milk, for example, and a breast pump device that uses the negative pressure transmitter.

BACKGROUND ART

A breast pump is conventionally used when a mother or the like pumps breast milk for an infant or the like and stores the pumped breast milk in a feeding bottle or the like.

So-called "manual breast pumps" and "electric breast pumps" exist as types of breast pumps.

A "manual breast pump" has a lever that swings when operated by an operator, and when the lever is swung, a negative pressure space is generated in a breast pump main body.

Using this negative pressure space, breast milk is drawn in and thus pumped from the mother's breast.

An "electric breast pump", on the other hand, does not have a lever that is operated by the operator and instead is configured such that a pump is driven by power from a motor or the like, a negative pressure space is generated in the breast pump main body by the pump, and using this negative pressure space, breast milk is drawn in and thus pumped from the mother's breast.

An "electric breast pump" is structured such that a negative pressure space is generated by suction power from the pump, and breast milk is drawn into this space. Hence, the breast milk may be suctioned into the pump side in error, and in this case, an electric component or the like such as the motor and so on breaks down or the like.

To avoid this situation, a configuration in which a "suction cup" or the like that serves as an example of a negative pressure transmitter is disposed in the breast pump main body and the pump suctions the atmosphere in the suction cup so as not to directly suction the atmosphere in a space communicating with the breast has been proposed (see PTL 1, for example).

More specifically, when the pump suctions the atmosphere in the suction cup, the suction cup collapses, whereby negative pressure is generated in the breast pump main body.

By employing the suction cup, the space that communicates with the breast does not communicate with the interior of the suction cup, which communicates with the pump and so on, and as a result, a situation in which breast milk is suctioned to the pump side in error can be forestalled.

CITATION LIST

Patent Literature

[PTL 1] U.S. Patent Application Publication No. 2016/0228624

SUMMARY OF INVENTION

Technical Problem

However, a problem occurs in that when suction by the pump is finished, the shriveled suction cup (the negative pressure transmitter) does not return to its original shape, and as a result, it may be impossible to generate sufficient negative pressure in the breast pump main body the next time suction is performed using the pump.

Moreover, depending on the shape of the shriveled suction cup (the negative pressure transmitter), a part thereof may frequently come into contact with the breast pump main body side, and as a result, a hole or the like may form in the contact part such that breast milk is suctioned to the pump side through the hole or the like.

Therefore, an object of the present invention is to provide a negative pressure transmitter, such as a suction cup, and a breast pump device that uses the negative pressure transmitter, with which the shape of the negative pressure transmitter remains constant when the negative pressure transmitter deforms, for example shrivels, so that no part thereof comes into contact with another member.

Solution to Problem

According to the present invention, the object described above is achieved by a negative pressure transmitter that includes an opening, a closed bottom portion, and an intermediate portion connecting the opening to the bottom portion, wherein the intermediate portion includes at least a plurality of rigid portions that are formed at predetermined intervals so as to inhibit deformation, and flexible portions that are formed between the plurality of rigid portions from a flexible material.

According to this configuration, the intermediate portion includes at least the plurality of rigid portions that are formed at predetermined intervals so as to inhibit deformation, and the flexible portions that are formed between the plurality of rigid portions from a flexible material.

Hence, the flexible portions are caused to deform, for example to shrivel, into a predetermined shape by the rigid portions. Therefore, a situation in which the negative pressure transmitter shrivels into various shapes and does not return to its original shape, as in the prior art, can be forestalled, and the negative pressure transmitter can be configured so as to always return to its original shape. As a result, negative pressure generated in a breast pump or the like to which the negative pressure transmitter is attached can be controlled appropriately.

Moreover, since the negative pressure transmitter always shrivels into the same shape, a situation in which a part or the like of the negative pressure transmitter frequently comes into contact with the side of a breast pump main body or the like such that a hole or the like forms in the contact part can be forestalled. As a result, a situation in which breast milk enters the negative pressure transmitter through this hole or the like and is suctioned or the like to the side of a pump or the like, for example, can be forestalled.

Preferably, the rigid portions and the flexible portions are formed to extend continuously from the intermediate portion to the bottom portion.

According to this configuration, the rigid portions and the flexible portions are formed to extend continuously from the intermediate portion to the bottom portion, and therefore the degree of deformation, for example shriveling, that occurs over the entire negative pressure transmitter can be increased. As a result, the negative pressure that is generated inside the breast pump or the like to which the negative pressure transmitter is attached can be increased. Further, by increasing the degree of shriveling, the likelihood of a part or the like of the negative pressure transmitter frequently coming into contact with the side of the breast pump main body or the like can be minimized.

Preferably, a support portion that inhibits deformation is provided in a central part of the bottom portion, and the rigid portions are formed in a rectilinear shape from the intermediate portion to the bottom portion and connected to the support portion.

According to this configuration, the rigid portions are formed in a rectilinear shape from the intermediate portion to the bottom portion and connected to the support portion in the central part of the bottom portion, and therefore, when the flexible portions deform, for example shrivel, along the rigid portions disposed in a rectilinear shape and the interior atmosphere is suctioned by the pump or the like, the rigid portions are twisted into a spiral shape about the support portion.

By twisting the negative pressure transmitter into a spiral shape in this manner, the overall volume thereof can be reduced, and as a result, greater negative pressure can be generated.

Further, by ensuring that the deformation state of the negative pressure transmitter is always a state of being "twisted into a spiral shape", the deformation can be kept constant, and the negative pressure transmitter can easily be returned to its original state.

Furthermore, by setting the negative pressure transmitter in a state of being "twisted into a spiral shape", the likelihood of a part or the like of the negative pressure transmitter frequently coming into contact with the side of the breast pump main body or the like can be minimized.

Preferably, no angular shapes are formed on at least the intermediate portion and the surface of the bottom portion.

According to this configuration, no angular shapes are formed on the intermediate portion and the surface of the bottom portion, and therefore, when the flexible portions and rigid portions deform, for example shrivel or twist, the deformation thereof is not impeded.

Preferably, the opening has a shape that corresponds to an attachment subject portion to which the opening is attached, and when the shape of the bottom portion differs from the shape of the opening, the shape gradually changes.

According to this configuration, the opening has a shape that corresponds to the attachment subject portion (a suction cap opening, for example) to which the opening is attached, and therefore a sealing property can be improved so that a negative pressure space can be generated effectively in the breast pump main body or the like.

By ensuring that when the shape of the bottom portion differs from the shape of the opening, the shape gradually changes, the opening can be formed in a shape that corresponds to the attachment subject portion regardless of the shape of the bottom portion.

Likewise, the bottom portion can be formed in any desired shape, regardless of the shape of the opening.

Preferably, a breast pump device comprises a breast disposing portion in which a breast portion, such as a breast and a nipple, of a subject is disposed, a breast pump main body portion including a negative pressure generation space, and the negative pressure generator described above.

Advantageous Effects of Invention

An advantage of the present invention is being able to provide a negative pressure transmitter, such as a suction cup, and a breast pump device that uses the negative pressure transmitter, with which the shape of the negative pressure transmitter remains constant when the negative pressure transmitter deforms, for example shrivels, so that no part thereof comes into contact with another member.

DESCRIPTION OF EMBODIMENTS

A preferred embodiment of the present invention will be described in detail below with reference to the figures.

Note that the embodiment described below is a preferred specific example of the present invention, and therefore various preferred technical limitations have been applied thereto. In the absence of wording specifically limiting the present invention in the following description, however, the scope of the present invention is not limited to these aspects.

Figure 1:
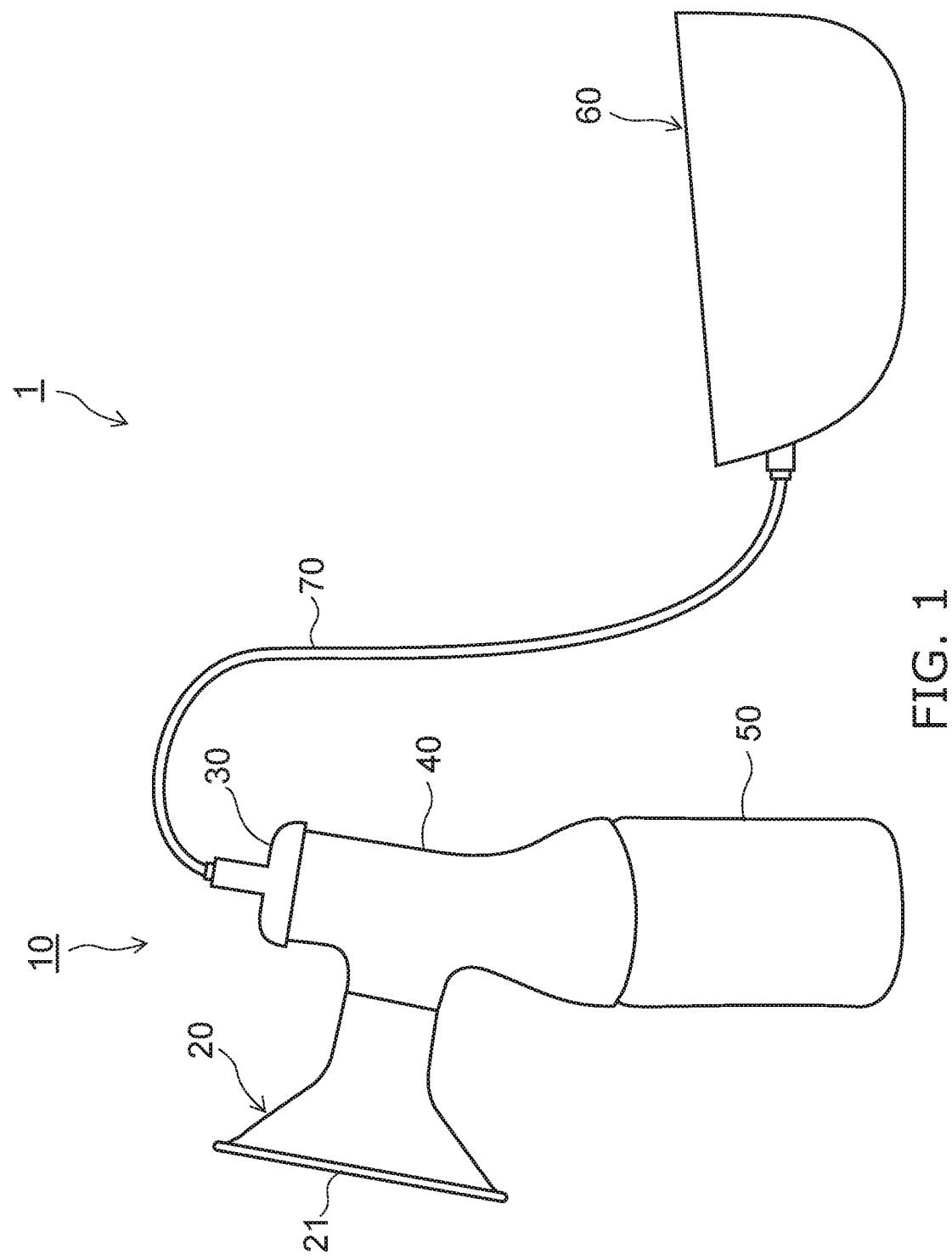
FIG. 1 is a schematic view showing main configurations of an electric breast pump including a breast pump that serves as an example of the breast pump device according to the present invention.

FIG. 1 is a schematic view showing main configurations of an "electric breast pump 1" including a "breast pump 10" that serves as an example of the breast pump device according to the present invention.

As shown in FIG. 1, the electric breast pump 1 includes the breast pump 10 and a pumping management device 60, the breast pump 10 and the pumping management device 60 being connected by a suction tube 70.

Further, the breast pump 10 includes a breast disposing portion 20, a breast pump main body 40 serving as an example of a breast pump main body portion, a feeding bottle 50, and a cap 30.

The respective configurations will be described below.

(Breast Disposing Portion 20)

As shown in FIG. 1, the breast pump 10 includes the breast disposing portion 20, in which the breast of a mother or the like serving as a user is disposed.

The breast disposing portion 20 has an overall funnel shape and includes an insertion port 21 into which the mother or the like inserts her breast.

Accordingly, an opening part of the insertion port 21 has the largest diameter, and the diameter gradually decreases.

(Breast Pump Main Body 40)

Figure 2:
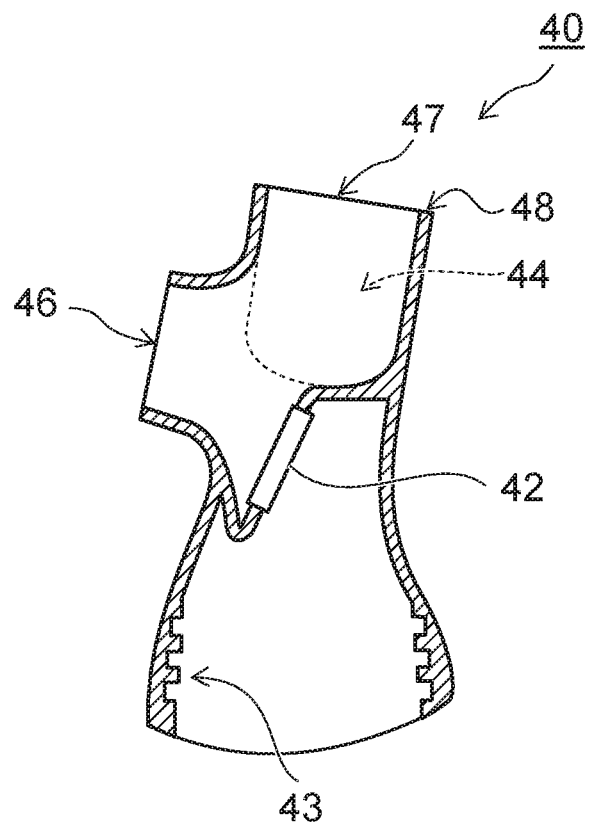
FIG. 2 is a schematic sectional view of a breast pump main body.

FIG. 2 is a schematic sectional view of the breast pump main body 40.

As shown in FIG. 2, a breast disposing portion opening 46 for attaching the breast disposing portion 20 shown in FIG. 1 is formed in the breast pump main body 40.

Further, a suction cup disposing portion 44 in which a first negative pressure space 45 and a "suction cup 80" to be described below, which is indicated by a dotted line in FIG. 2, are disposed is formed in a space connected to the breast disposing portion opening 46.

Furthermore, a suction cup opening 47 that serves as an example of an attachment subject portion for inserting the suction cup 80, which serves as an example of a negative pressure transmitter to be described below, is formed in the breast pump main body 40.

Further, as shown in FIG. 2, a check valve 42 is disposed in the breast pump main body 40, and a breast pump main body-side screw portion 43 for screwing in the feeding bottle 50 shown in FIG. 1 is formed in a lower portion of the breast pump main body 40.

The check valve 42 of FIG. 2 is configured so that only an inflow of breast milk from the breast disposing portion opening 46 is allowed to travel to the breast pump main body-side screw portion 43 side, while backflow is impeded.

(Feeding Bottle 50)

As shown in FIG. 1, the feeding bottle 50 is connected detachably to the breast pump main body 40, and the feeding bottle 50 is configured to store breast milk pumped by the breast pump 10 shown in FIG. 1.

Further, a feeding bottle-side screw portion is formed in an opening, not shown in the figures, in an upper portion of the feeding bottle 50, and by screwing the feeding bottle-side screw portion to the breast pump main body-side screw portion 43 shown in FIG. 2, the feeding bottle 50 is attached to the breast pump main body 40.

(Cap 30)

As shown in FIGS. 1 and 2, the cap 30 is disposed to cover the suction cup opening 47 of the breast pump main body 40.

More specifically, the cap 30 is configured such that when the suction cup 80 is disposed in the suction cup disposing portion 44 shown in FIG. 2, the cap 30 is disposed thereon, and in so doing, the suction cup 80 can be attached to the breast pump main body 40 in an airtight state.

Figure 3:
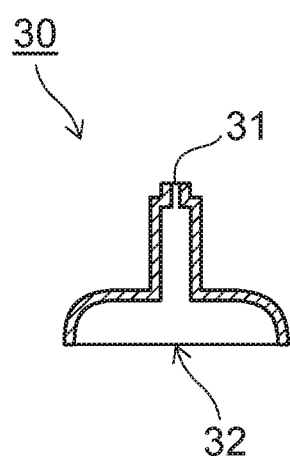
FIG. 3 is a schematic sectional view of a cap.

FIG. 3 is a schematic sectional view of the cap 30.

As shown in FIG. 3, a suction tube attachment portion 31 is formed on an upper portion thereof, and a through hole is formed in an upper end thereof.

Further, a cap lower portion opening 32 is formed in a lower portion of the cap 30.

As shown in FIG. 3, a space is formed in the interior of the cap 30 so that the through hole in the suction tube attachment portion 31 can communicate with the cap lower portion opening 32.

(Pumping Management Device 60)

The pumping management device 60 shown in FIG. 1 includes in the interior thereof a motor, a pump, and so on, not shown in the figures, and by driving the motor and the pump, an atmosphere is suctioned into the suction tube 70 connected thereto.

More specifically, when the suction cup 80 is disposed in the suction cup disposing portion 44 of the breast pump main body 40 shown in FIG. 2 and covered by the cap 30, as shown in FIG. 1, the atmosphere in the suction cup 80 is suctioned by the suction of the pumping management device 60.

Figure 4:
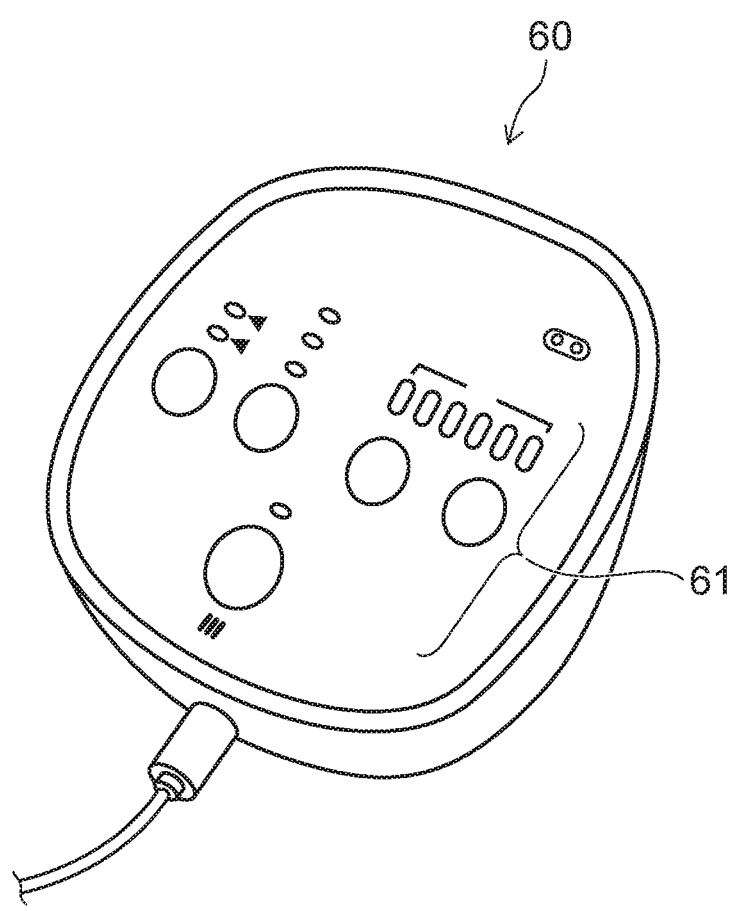
FIG. 4 is a schematic view showing an upper surface of a pumping management device of FIG. 1.

FIG. 4 is a schematic view showing an upper surface of the pumping management device 60 of FIG. 1.

As shown in FIG. 4, various operation input portions 61 such as switches, for example, are disposed on the surface of the pumping management device 60.

Thus, when an operator operates these switches and other various operation input portions 61, operations of the motor and so on can be controlled.

(Configuration of Enclosed Space S in Breast Pump Main Body 10, Pumping Operation, and so on)

Figure 5:
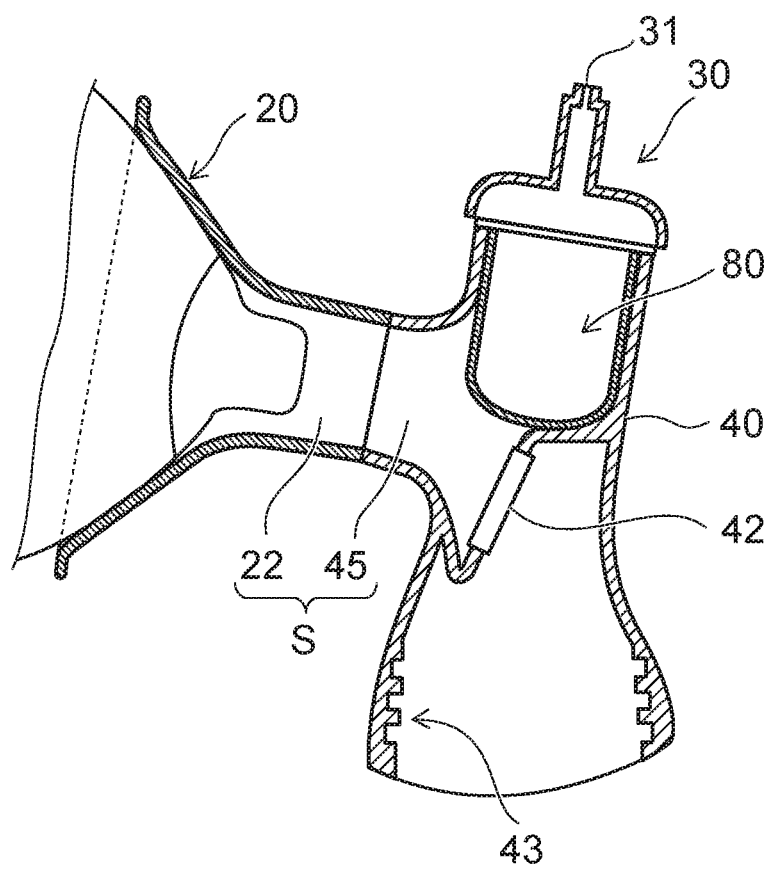
FIG. 5 is a schematic sectional view showing main configurations of a breast disposing portion when a breast is disposed therein, the breast pump main body, a suction cup, and the cap of the electric breast pump shown in FIG. 1.

FIG. 5 is a schematic sectional view showing the main configurations of the breast disposing portion 20 when a breast is disposed therein, the breast pump main body 40, the suction cup 80, and the cap 30 of the electric breast pump 1 shown in FIG. 1.

As shown in FIG. 5, when the user disposes her breast in the breast disposing portion 20, an enclosed space S is formed by a second negative pressure space 22 and a first negative pressure space 45, which are the parts of the breast disposing portion 20 in which the breast is not disposed.

Hence, when the pumping management device 60 of FIG. 1 is operated such that the atmosphere in the suction cup 80 of FIG. 5 is suctioned through the suction tube 70 and the cap 30 and the suction cup 80 shrivels, the volume of the enclosed space S of FIG. 5 increases in an enclosed state, and a "negative pressure state" is established in the enclosed space S.

As a result, breast milk is pumped from the breast disposed in the breast disposing portion 20 of FIG. 5.

The breast milk pumped in this manner passes through the check valve 42 when the negative pressure state in the enclosed space S is released, and is stored in the feeding bottle 50 shown in FIG. 1.

Hence, the electric breast pump 1 according to this embodiment is configured such that only the suction tube 70, the cap 30, and the suction cup 80 communicate with the pumping management device 60, which includes electric components and so on, and therefore breast milk inflow or the like into the suction cup 80 does not occur.

As a result, situations in which some of the breast milk is suctioned to the side of the pumping management device 60, which includes electric components and so on, causing a breakdown or the like, can be effectively prevented.

(Suction Cup 80)

Next, the configuration of the "suction cup 80" of FIG. 5, which is the main feature of this embodiment, will be described in detail.

Figure 6:
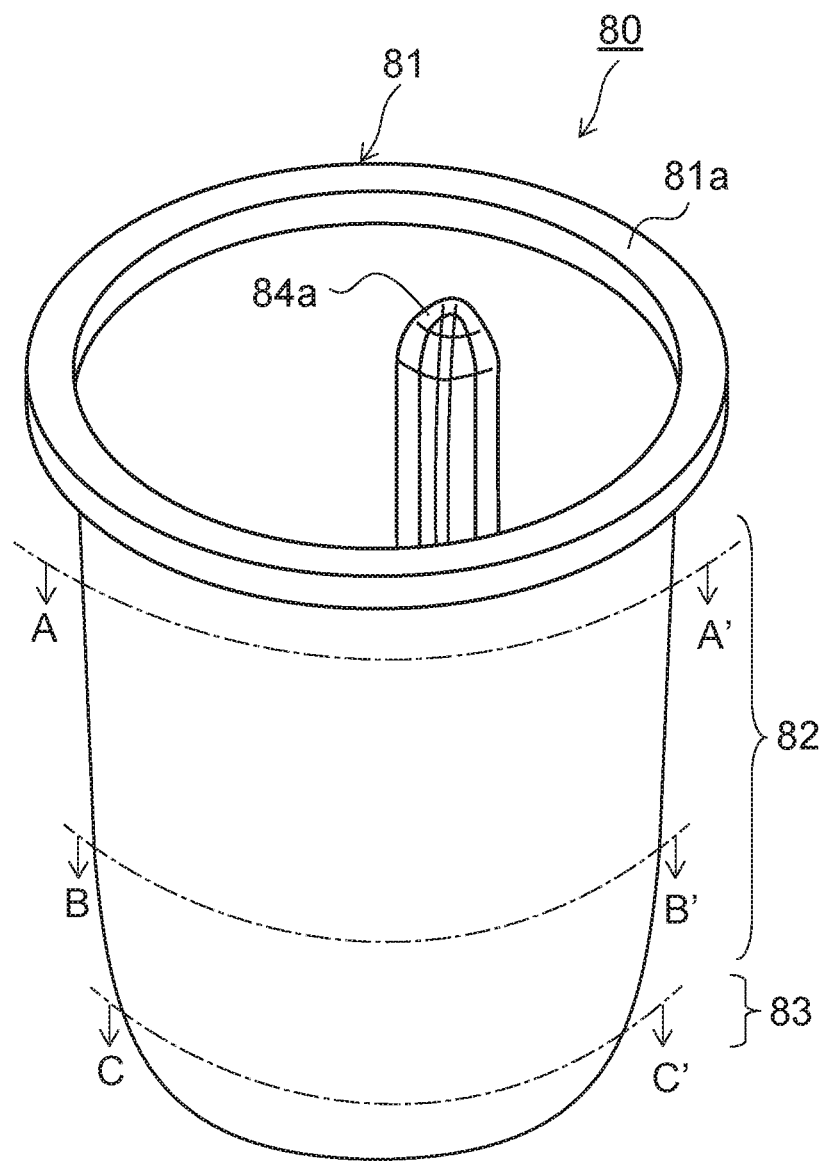
FIG. 6 is a schematic perspective view showing the suction cup.

FIG. 6 is a schematic perspective view showing the suction cup 80.

As shown in FIG. 6, the suction cup 80 has an overall vertically long bag shape with an opening in the upper portion and a closed bottom portion.

The suction cup 80 is formed entirely from a flexible material, for example an elastomer or the like such as silicone rubber, isoprene rubber, or SEBS (styrene-ethylene-butylene-styrene).

More specifically, as shown in FIG. 6, an opening 81 is provided in the upper portion, and a closed bottom portion 83 is provided in the lower portion. An intermediate portion 82 is formed between the opening 81 and the bottom portion 83.

As shown in FIG. 6, a substantially circular opening, for example, is formed as the opening 81. Further, a ring-shaped edge portion 81a formed to project outward is formed on a peripheral edge of the opening.

The shape of the opening is formed to correspond to the shape and size of the suction cup opening 47 of the breast pump main body 40 shown in FIG. 2.

In other words, since in this embodiment, the suction cup opening 47 of FIG. 2 is substantially circular, the opening is formed to be substantially circular in accordance therewith and has a similar size (diameter) thereto.

By forming the opening in this shape, when the suction cup 80 is disposed in the suction cup disposing portion 44 of FIG. 2, the shape and size (diameter) of the opening of the suction cup 80 match those of the suction cup disposing portion 44, and therefore the suction cup 80 can be disposed in the suction cup opening 47 without gaps.

Further, by disposing the upper edge portion 81a shown in FIG. 6 appropriately on a breast pump main body upper edge portion 48 shown in FIG. 2 and attaching the cap 30 shown in FIG. 5 so as to sandwich the upper edge portion 81a, a sealing property for keeping the enclosed space S of FIG. 2 in an enclosed state can be improved.

Figure 7:
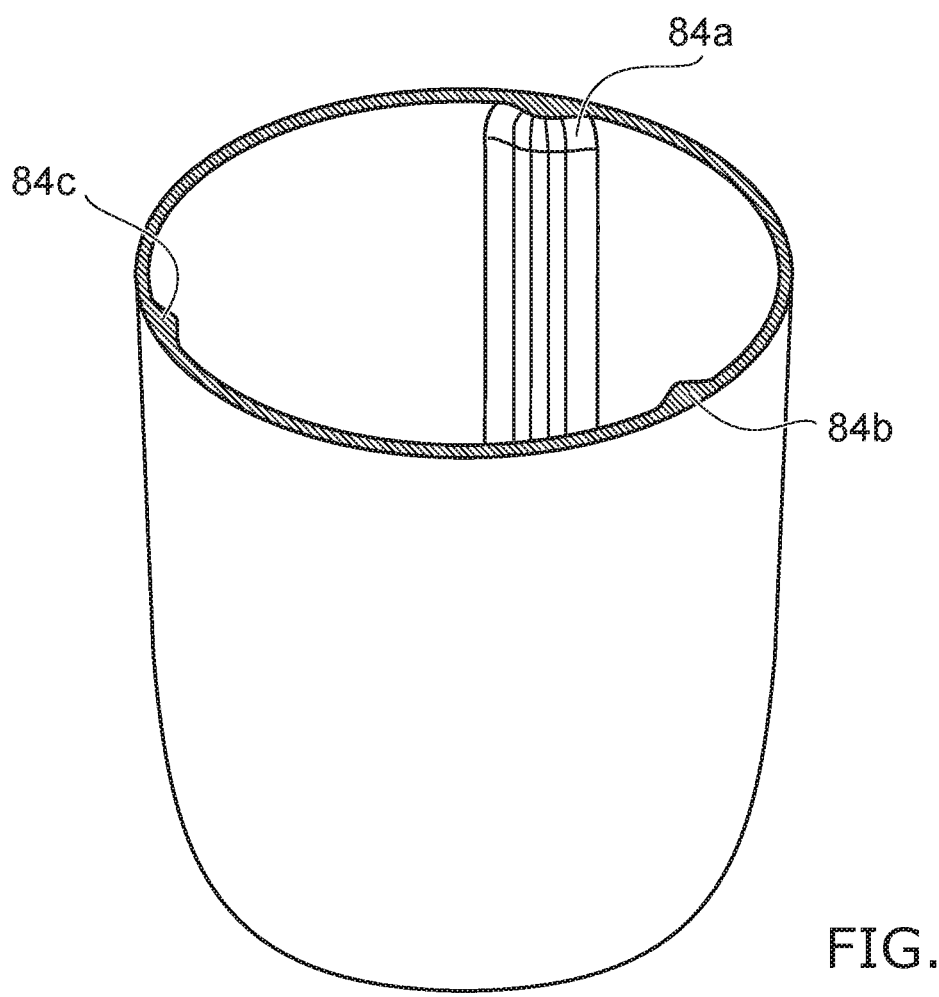
FIG. 7 is a schematic sectional view taken along an A-A' line in FIG. 6.
Figure 8:
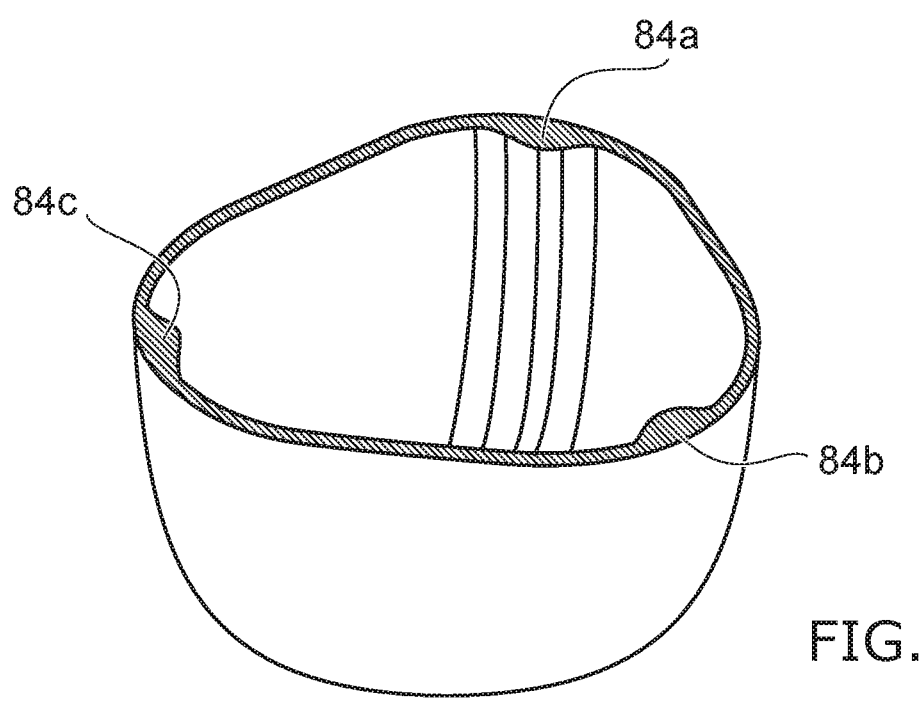
FIG. 8 is a schematic sectional view taken along a B-B' line in FIG. 6.
Figure 9:
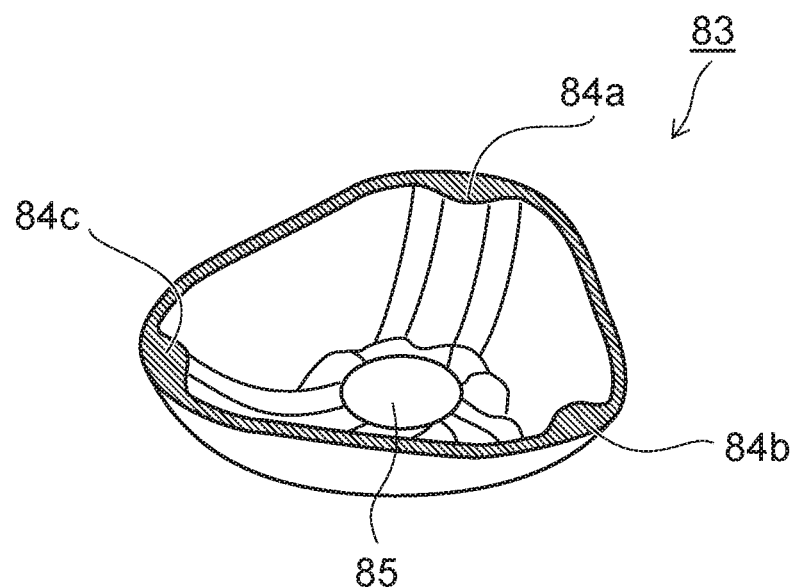
FIG. 9 is a schematic sectional view taken along a C-C' line in FIG. 6.

FIG. 7 is a schematic sectional view taken along an A-A' line in FIG. 6, FIG. 8 is a schematic sectional view taken along a B-B' line in FIG. 6, and FIG. 9 is a schematic sectional view taken along a C-C' line in FIG. 6.

As shown in FIGS. 7 to 9, three ribs 84a, 84b, 84c serving as examples of rigid portions that produce an action for inhibiting deformation are formed in a rectilinear shape inside the suction cup 80 so as to extend in a vertical direction in the figure (a longitudinal direction of the suction cup 80) from the intermediate portion 82 to the bottom portion 83 in FIG. 6.

Further, as shown in FIG. 9, a circular support portion 85 serving as a rigid portion that also produces an action for inhibiting deformation is formed in a central part of the inside of the bottom portion 83.

As shown in FIG. 9, the three ribs 84a, 84b, 84c are connected to the support portion 85.

Figure 10:
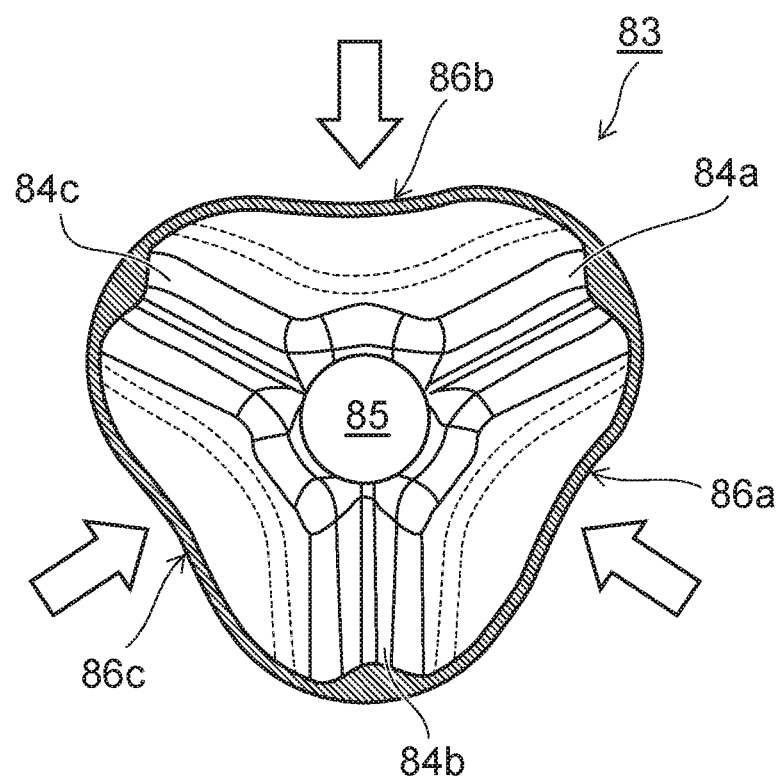
FIG. 10 is a schematic view showing a configuration on the inside of a bottom portion of FIG. 9 from above.

FIG. 10 is a schematic view showing the configuration on the inside of the bottom portion 83 of FIG. 9 from above.

As shown in FIG. 10, in the bottom portion 83, the overall shape differs from the substantially circular shape of the opening and instead is a shape approximating a triangle, for example;

More specifically, parts between the three ribs 84a, 84b, 84c serving as rigid portions form flexible portions 86a, 86b, 86c that deform easily, and these flexible portions 86a etc. are configured to deform, for example to shrivel, easily toward the inside of the suction cup 80.

Therefore, the overall shape approximates a triangle.

Hence, in this embodiment, the opening 81 shown in FIG. 6 is substantially circular and the bottom portion 83 shown in FIG. 10 has a shape approximating a triangle, and therefore the opening 81 and the bottom portion 83 are configured to have completely different shapes.

In other words, in this embodiment, the shape "gradually changes" from the opening 81 toward the bottom portion 83.

Therefore, in a case where the opening 81 is preferably substantially circular from the point of view of the sealing property and the bottom portion 83 is preferably non-circular from the point of view of ease of deformation, for example shriveling, a shape that meets these requirements can be realized.

Further, the surface of the suction cup 80 according to this embodiment has a smooth shape with no angular portions.

Therefore, when the flexible portions 86a, 86b, 86c of FIG. 10 deform or the like inwardly so as to shrivel as a whole, the deformation thereof is not impeded.

In this embodiment, the bottom portion 83 has a shape approximating a triangle, but the present invention is not limited thereto, and a square or other polygonal shape may be employed instead.

(Example Operation of Electric Breast Pump 1)

An example in which a mother pumps breast milk for an infant using the electric breast pump 1 according to this embodiment will be described below.

First, the mother who is intending to execute breast milk pumping inserts and disposes her breast into the insertion port 21 of the breast disposing portion 20 of the breast pump 10 shown in FIG. 1.

Next, by operating the switches constituting the various operation input portions 61 of FIG. 4, the mother selects the desired operation.

Normally, in the electric breast pump 1, an operation for suctioning and releasing the breast alternately and repeatedly is executed. In this embodiment, for example, the mother selects a setting for aligning the repetition interval with the interval of the "pulse".

Hence, the motor and the pump of the pumping management device 60 of FIG. 1 are driven in accordance with the rhythm of the pulse.

First, the pump is driven to perform a suction process.

More specifically, the atmosphere in the suction cup 80 shown in FIG. 5 is suctioned through the suction tube 70 shown in FIG. 1.

Accordingly, the parts corresponding to the flexible portions 86a, 86b, 86c shown in FIG. 10 deform toward the inside of the suction cup 80 so as to shrivel up to dotted line parts shown in FIG. 10, for example.

Figure 11:
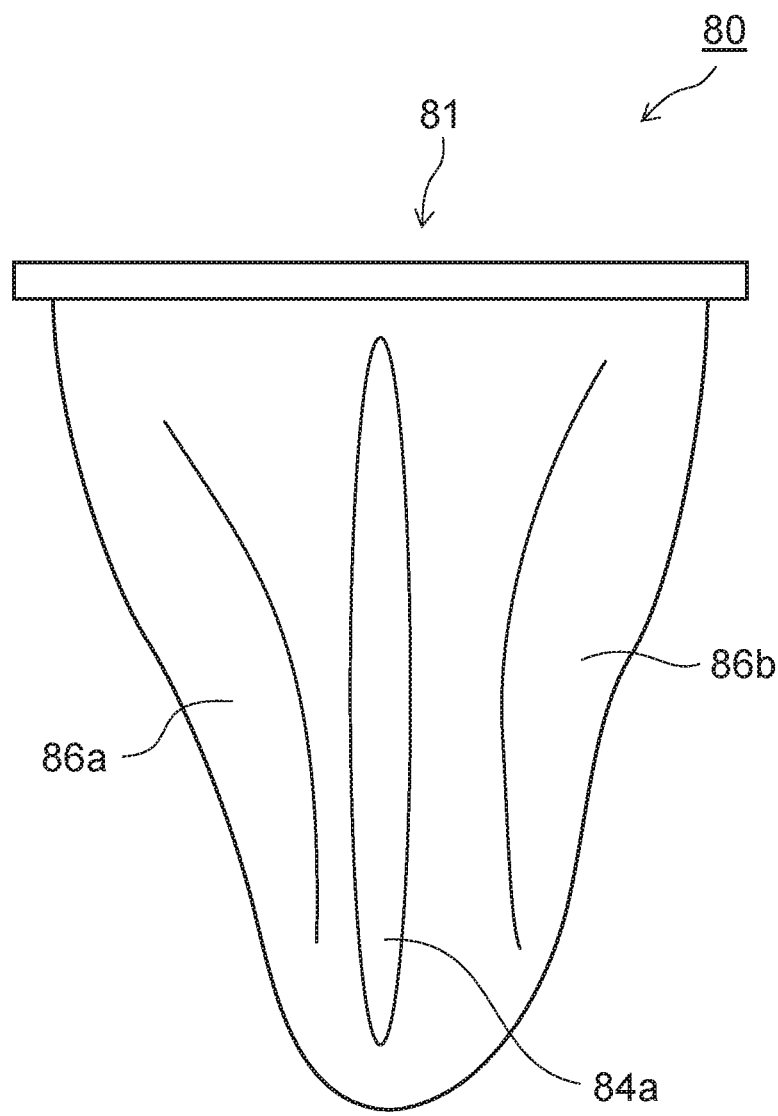
FIG. 11 is a schematic illustrative view showing the suction cup in a deformed state, for example a shriveled state, after being suctioned by a pump.

FIG. 11 is a schematic illustrative view showing the suction cup 80 in a deformed state, for example a shriveled state, after being suctioned by the pump.

In this embodiment, the ribs 84a etc. are provided, and therefore these parts do not shrivel. Hence, only the flexible portions 86a, 86b, 86c formed between the ribs 84a etc. shrivel inwardly as indicated by the dotted lines in FIG. 10.

The initial deformation state shown in FIG. 11 is always the same and does not vary every time suction is performed.

When suction is performed further by operating the pumping management device 60 from the deformation state of FIG. 11, inward shriveling of the flexible portions 86a, 86b, etc. shown in FIG. 11 progresses to the maximum extent, whereby the flexible portions 86a etc. stick to the rectilinearly disposed ribs 84a etc.

When suction is executed even further, the operation advances to the next stage, in which the shriveled flexible portions 86a etc. are twisted into a spiral shape about the support portion 85 of FIG. 10.

Figure 12:
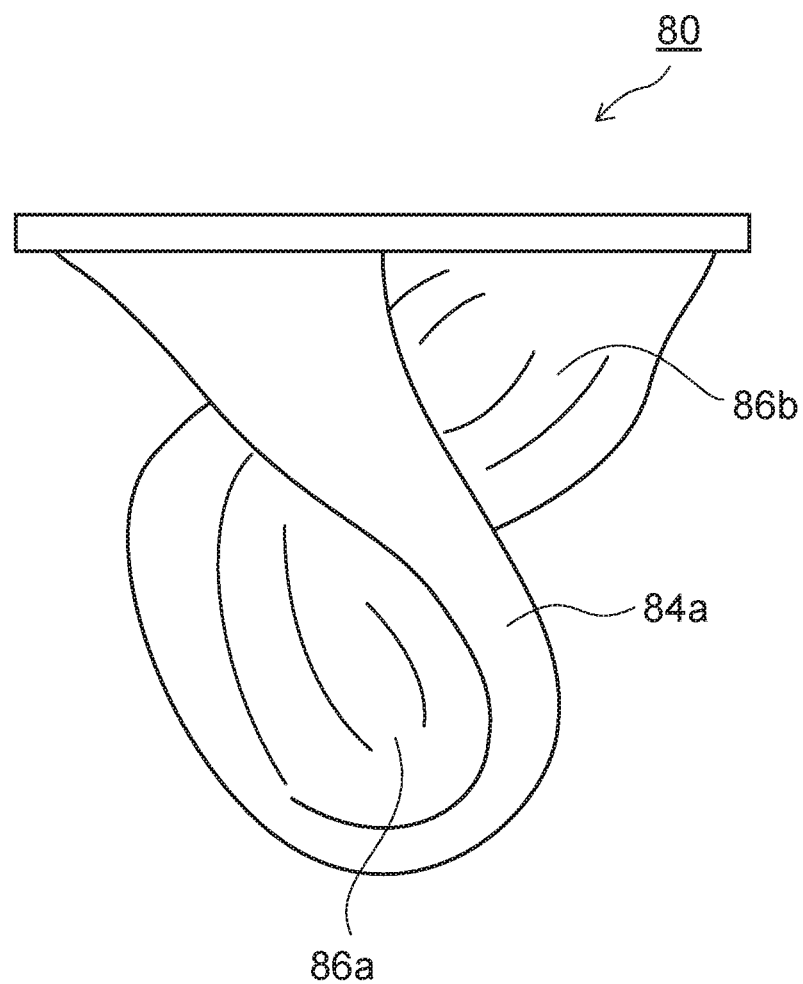
FIG. 12 is a schematic view showing a state in which the suction cup is twisted into a spiral shape.

FIG. 12 is a schematic view showing a state in which the suction cup 80 is twisted into a spiral shape.

Hence, in this embodiment, the flexible portions 86a etc., which are the first parts of the suction cup 80 to deform, shrivel in response to suction by the pump, whereupon the ribs 84a etc. and the flexible portions 86a etc. are both twisted into a spiral shape. Moreover, the spiral shape is always the same.

Next, when suction by the pump is stopped and released, the suction cup 80 twisted into the spiral shape shown in FIG. 12 returns to the shape shown in FIG. 6 via a reverse process.

Next, when suction by the pump restarts, the suction cup 80 is twisted into the spiral shape shown in FIG. 12 via the same processes as those described above.

Hence, in this embodiment, in contrast to the prior art, the suction cup 80 deforms into a deformation state that can easily be returned to the original state, and as a result, the suction cup 80 always returns to its original shape when suction by the pump is released.

Further, in this embodiment, the flexible portions 86*a* etc. shrivel along the rectilinear ribs 84*a* etc. and are then twisted into a spiral shape, and therefore the volume (capacity) of the suction cup 80 can be minimized.

Hence, the enclosed space S in the breast pump main body 40 shown in FIG. 5 can be increased, and as a result, greater negative pressure can be generated.

Further, as shown in FIGS. 11 and 12, the suction cup 80 deforms so as to shrivel in a direction separating from the wall surface of the breast pump main body 40 on the outside of the suction cup 80 and is twisted into a spiral shape while remaining in the same separated state. As a result, a situation in which a part or the like of the suction cup 80 frequently comes into contact with the wall surface or the like of the breast pump main body 40 such that a hole forms therein can be forestalled.

The present invention is not limited to the above embodiment and may be subjected to various modifications within a scope that does not depart from the claims.

REFERENCE SIGNS LIST

1 Electric breast pump
20 Breast disposing portion
21 Insertion port
22 Second negative pressure space
30 Cap
31 Suction tube attachment portion
32 Cap lower portion opening
40 Breast pump main body
50 Feeding bottle
40 Breast pump main body
42 Check valve
43 Breast pump main body-side screw portion
44 Suction cup disposing portion
45 First negative pressure space
46 Breast disposing portion opening
47 Suction cup opening
48 Breast pump main body upper edge portion
60 Pumping management device
61 Various operation input portions
70 Suction tube
80 Suction cup
81 Opening
81*a* Edge portion
82 Intermediate portion
83 Bottom portion
84*a*, 84*b*, 84*c* Ribs
85 Support portion
86*a*, 86*b*, 86*c* Flexible portions
S Enclosed space

The invention claimed is:

1. A breast pump device comprising:
a breast disposing portion that is configured to receive a breast portion, such as a breast and a nipple of a subject, disposed therein;
a breast pump main body portion that includes a negative pressure generation space; and
a negative pressure transmitter that is configured to create a negative pressure in the negative pressure generation space, wherein
the negative pressure transmitter is formed of an elastic material to be collapsible and has a roughly columnar shape extending in an axis direction with an inner hollow, having an opening in a substantially circular shape at one end in the axis direction, a closed bottom portion at an other end, and an intermediate portion that connects the opening to the closed bottom portion,
the intermediate portion is composed with a plurality of ridge portions and a plurality of flexible portions, wherein the plurality of flexible portions number the same as the plurality of ridge portions and are arranged to alternate with the plurality of ridge portions in a circumferential direction around the axis direction wherein the plurality of ridge portions are formed as ribs protruding along a radial direction based on the axis direction, the plurality of ridge portions having a thickness greater than a thickness of the plurality of flexible portions and configured to inhibit deformation compared to the plurality of flexible portions,
a support portion has a circular shape in an axis view that is in the axis direction, and is provided in a central part of the bottom portion to cover the central part wherein the support portion has a larger thickness than a remainder of the bottom portion and is configured to inhibit deformation compared to the remainder of the bottom portion,
the plurality of ridge portions extending linearly from the intermediate portion to the bottom portion and connected to the support portion, and
when an interior atmosphere of the inner hollow of the negative pressure transmitter is suctioned to be under a negative pressure, the intermediate portion of the negative pressure transmitter is twisted into a spiral shape about the support portion such that the negative pressure of the negative pressure transmitter is transmitted to the negative pressure generation space.

2. The breast pump device according to claim 1, wherein
the opening of the negative pressure transmitter has the substantially circular shape, from the axis view, that corresponds to an attachment subject portion to which the opening is attached,
the bottom portion has a shape that is different from the substantially circular shape of the opening from the axis view, and
the roughly columnar shape of the negative pressure transmitter changes gradually from the opening to the bottom portion such that an outer circumference of the negative pressure transmitter is smoothly connected from the opening to the bottom portion.

3. The breast pump device according to claim 2, wherein the shape of the bottom portion approximates a triangle.

4. The breast pump device according to claim 1, wherein the plurality of ridge portions and the plurality of flexible portions of the negative pressure transmitter are formed to extend continuously from the intermediate portion to the bottom portion.

5. The breast pump device according to claim 4, wherein none of the plurality of ridge portions of the negative pressure transmitter extends to the opening.

6. The breast pump device according to claim 5, wherein the plurality of ridge portions protrude inwardly from an inner circumference of the intermediate portion.

7. The breast pump device according to claim 1, wherein the plurality of ridge portions protrude inwardly from an inner circumference of the intermediate portion.

8. The breast pump device according to claim 1, wherein the plurality of ridge portions are arranged with equal intervals in the circumferential direction.

9. The breast pump device according to claim 1, wherein the bottom portion and the support portion are integrally formed of a similar material.

10. The breast pump device according to claim 9, wherein the intermediate portion and the bottom portion are integrally formed of the similar material.

11. The breast pump device according to claim 1, wherein the intermediate portion and the bottom portion are integrally formed of a similar material.

* * * * *